United States Patent [19]

Kashy et al.

[11] Patent Number: 4,736,106

[45] Date of Patent: Apr. 5, 1988

[54] METHOD AND APPARATUS FOR UNIFORM CHARGED PARTICLE IRRADIATION OF A SURFACE

[75] Inventors: Edwin Kashy, Haslett; Bradley M. Sherrill, Okemos, both of Mich.

[73] Assignee: Michigan State University, East Lansing, Mich.

[21] Appl. No.: 916,387

[22] Filed: Oct. 8, 1986

[51] Int. Cl.$^4$ .............................................. G21K 1/093
[52] U.S. Cl. ...................... 250/396 ML; 250/396 R; 250/492.3
[58] Field of Search ........... 250/396 ML, 396 R, 398, 250/306, 307, 310, 492.3

[56] References Cited

U.S. PATENT DOCUMENTS 3,028,491  4/1962  Schleich ............................. 250/396
3,482,136 12/1969  Herrera ............................... 250/396

OTHER PUBLICATIONS

E. Segré, *Nuclei and Particles*, W. A. Benjamin, Inc., New York, pp. 39–49, (1969).
Koehler et al., Medical Physics, 4, 297, (1977).
D. Cary, 'Turtle', Fermi Nat'l. Accelerator Lab., Report 64-2041.000.

*Primary Examiner*—Carolyn E. Fields
*Assistant Examiner*—John A. Miller
*Attorney, Agent, or Firm*—Ian C. McLeod

[57] ABSTRACT

A method and apparatus which uses combined quadrupole (Qx and Qy) and multipole magnet sets (Mx and My) to focus a charged particle beam from a point source is described. Primarily the multipole magnet sets are octupole magnets. The apparatus is particularly useful for providing a uniform intensity for ion implantation, in cancer therapy and in other fields where uniform charged particle irradiation of a surface is important.

6 Claims, 8 Drawing Sheets

METHOD AND APPARATUS FOR UNIFORM CHARGED PARTICLE IRRADIATION OF A SURFACE

BACKGROUND OF THE INVENTION

(1) Field of the Invention

The present invention relates to a method and apparatus which uses combined quadrupole and multipole, primarily octupole, magnet sets to increase the uniformity of a beam used in irradiating large targets or surfaces with charged particles in the beam. In particular the present invention relates to the use of the method and apparatus for ion implantation, for charged particle cancer therapy, for determining radiation effects on biological systems and radiation material damage studies, and for heavy ion irradiation of foils to produce microfilters.

(2) Prior Art

A beam of charged particles of large spatial dimensions with uniform cross-sectional or areal densities at a given location is essential in radiation treatments of tumors, as well as for many other applications. A simple method for the preparation of such a beam is to send the beam from an accelerator through a thin scattering target. The multiple scattering of the beam, which arises mainly from the interaction of the projectile with the nuclear charge of the target nuclei, results in an approximately gaussian angular distribution of the particles emerging from the target along the longitudinal axis of the beam (E. Segre, Nuclei and Particles, (W. A. Benjamin, Inc., New York p39–49 (1965)). By moving the position where irradiation is to take place far from the beam spreading target, the radiation field is enlarged and uniformity of dose is obtained at the cost of intensity.

Two methods have been discussed by Koehler, Sneider and Sisterson (A. M. Koehler, R. J. Schneider and J. M. Sisterson, Medical Physics 4, 297 (1977)) to improve the intensity of radiation fields for a given homogeneity. In the first method a narrow beam is swept over a target. A potential problem is the failure of the sweeper, which could result either in injury to the patient or in damage to material. In the second method, a double scattering scheme, one adds an additional beam spreading target downstream from the first target, with the second target appropriately obstructed near the center on the axis. The net result is an improvement of the flatness of the distribution over a certain irradiation area. A calculation using the double scattering system with a variable circular obstruction before the second scattering indicates a uniformity in the measuring plane of 10% with an efficiency for about 32%, which is considered satisfactory for medical treatment. However, when the scatterings occur within a beam transport or analysis system, a potential weakness of the double multiple-scattering method is the enlargement of the effective object size of the system by the second scattering and the increased loss of intensity due to nuclear interactions.

OBJECTS

It is therefore an object of the present invention to provide a method and apparatus for focussing a beam having a gaussian-like angular distribution, to produce a uniform beam without significantly reducing the beam intensity. Further, it is an object of the present invention to provide an apparatus which is simple and economical to construct and adjust. These and other objects will become increasingly apparent by reference to the following description and the drawings.

IN THE DRAWINGS

FIG. 1A shows the x-envelope of a beam and FIG. 1B shows the y-envelope of the beam in the apparatus of the present invention. The positions of octupole sets Mx and My, used to homogenize the particle areal density, are shown at the waists (areas of minimum beam size) FA1 and FA2 of the system.

In FIGS. 4A and 4B, the octupoles Mx and My were not used. In FIGS. 4C and 4D the octupoles Mx and My were turned on and adjusted to homogenize the distribution of the particles in the beam. The fluctuation in the curves reflect the statistical nature of the sampling of particles trasversing the system. A set of slits before the first quadrupole set limits the acceptance of the system to 80%.

In FIGS. 6A and 6B, the octupoles Mx and My were not used. In FIGS. 6C and 6D, the octupoles Mx and My have been turned on and adjusted to homogenize the distribution of the particles. The fluctuation in the curves reflect the statistical nature of the sampling of particles traversing the system. The slits at the entrance of the system limits the acceptance distribution in theta and phi, so that approximately 73% of the initial distribution is used.

GENERAL DESCRIPTION

The present invention relates to a magnetic optical beam homogenizing and focussing apparatus for charged particle beams which comprises: holder means adapted to mount on a source of accelerated charged particles which are scattered outward in a gaussian-like angular distribution from a longitudinal axis from the source, wherein an X and a Y axis are defined perpendicular to the longitudinal axis; beam transport magnetic lens sets positioned on the holder around the longitudinal axis, such that the beam of charged particles is focussed towards and crosses the longitudinal axis to define a focal area on the axis wherein the focal area of the beam viewed on the X axis is at a different part of the longitudinal axis than the focal area on the beam viewed on the Y axis; and at least two multipole magnet sets having at least 6 poles mounted on the holder around the longitudinal axis at each of the focal area on the X and Y axis, wherein the multipole magnet, depending upon the number of poles, make specific changes to the direction of the particles according to the position of the particles within the multipole.

Further the present invention relates to a method for focussing a beam of charged particles on a surface to be irradiated which comprises providing a holder means mounted on a point source of accelerated charged particles which are scattered outward in a gaussian-like angular distribution from a longitudinal axis from the source wherein an X and a Y axis are defined perpendicular to the longitudinal axis; beam transport magnetic lens sets positioned on the holder around the longitudinal axis, such that the beam of charged particles is focussed towards and crosses the longitudinal axis to define a focal area on the axis wherein the focal area of the beam viewed on the X axis is at a different part of the longitudinal axis than the focal area on the beam viewed on the Y axis; at least two multipole magnet sets having at least 6 poles mounted on the holder around the longitudinal axis at each of the focal area on the X and Y axis, wherein the multipole magnet sets, depending upon the number of poles, make specific changes to the direction of the particles according to the position of the particles within the multipole.

The present invention thus relates to use of non-linear magnetic optics to transform a large fraction of particles which have a gaussian-like areal distribution into a more uniform distribution. Calculations using the magnetic-optics computer code TURTLE (D. Cary, 'TURTLE', Fermi National Accelerator Laboratory, Report 64-2041.000) prove that the method achieves excellent homogeneity in the measuring plane with high beam efficiency.

SPECIFIC DESCRIPTION

FIGS. 1A, 1B, 2A, 2B and 3 show a holder 10 for quadrupole magnet sets Qx and Qy and for multipole, primarily octupole, magnet sets Mx and My. The charged particle beam originates at point P from a target (not shown) or other ion source of charged particles from an accelerator (not shown) where the charged particles have a gaussian-like angular distribution outward from the source along longitudinal axis m. The moving particles are bent by quadrupole magnet sets Qx and Qy as shown by imaginary envelopes ex1 and ex2 and ey1. The beam is then focussed by multipole magnet sets Mx and My to form envelopes emx and emy emanating from waist FA1 and FA2. In order to produce the envelopes ex1, ex2, ey, emx and emy the quadrupole magnet sets Qx and Qy and multipole magnet sets Mx and My preferably have field strengths as follows at 5 centimeters from their axes, first Qx: 7.33 kilogauss
Qy: −9.57 kilogauss
Second Qx: 5.41 kilogauss
my: −3.94 kilogauss
mx: 8.37 kilogauss Thus the method and apparatus makes use of magnetic lenses of high order, with octupole magnet sets Mx and My for symmetric distribution. The octupole magnet sets Mx and My are placed at the positions where waists (minimum beam size areas) FA1 and FA2 in the beam envelope ex1, ex2, ey1, emx and emy are located. A charged particle beam from an accelerator (not shown) is focussed at position P, where depending on the requirements, either: (1) a scatterer or target (T) of the atomic number Z and thickness is located, or (2) the beam from the accelerator is focussed. A beam defining slit P follows immediately and acts as the object of the quadrupole set Qx and Qy doublet. The tails of the beam divergence entering the quadrupole doublet set Qx and Qy can be limited by the slit, placed ahead of the first quadrupole set.

Figure 1A:
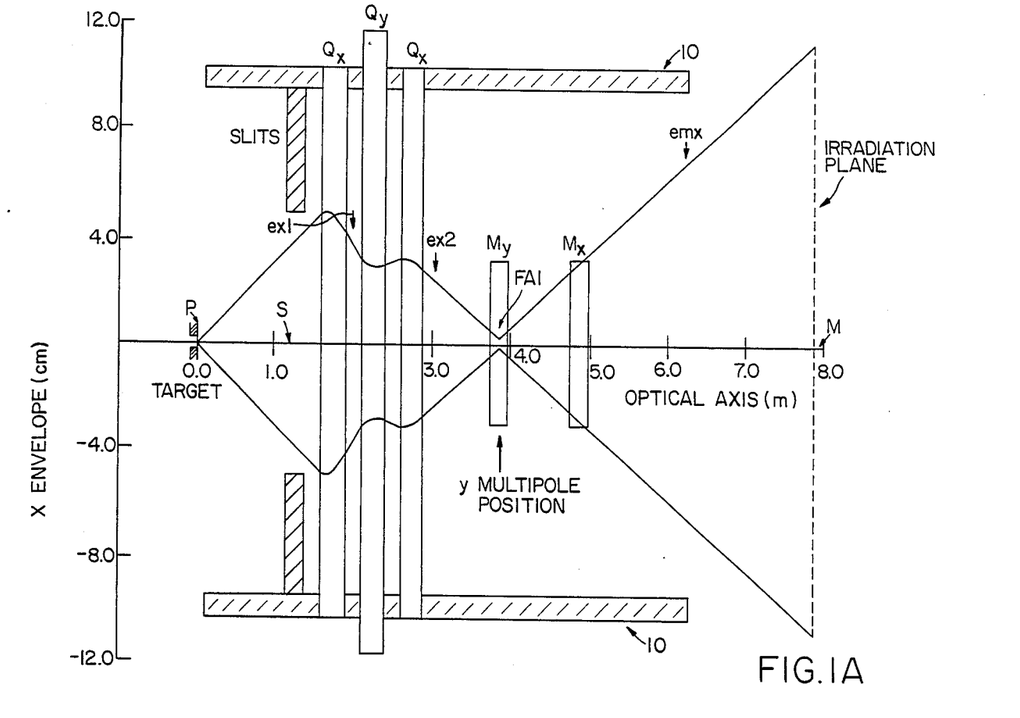
FIGS. 1A and 1B are front cross-sectional views of a sample apparatus which uses the present invention.
Figure 1B:
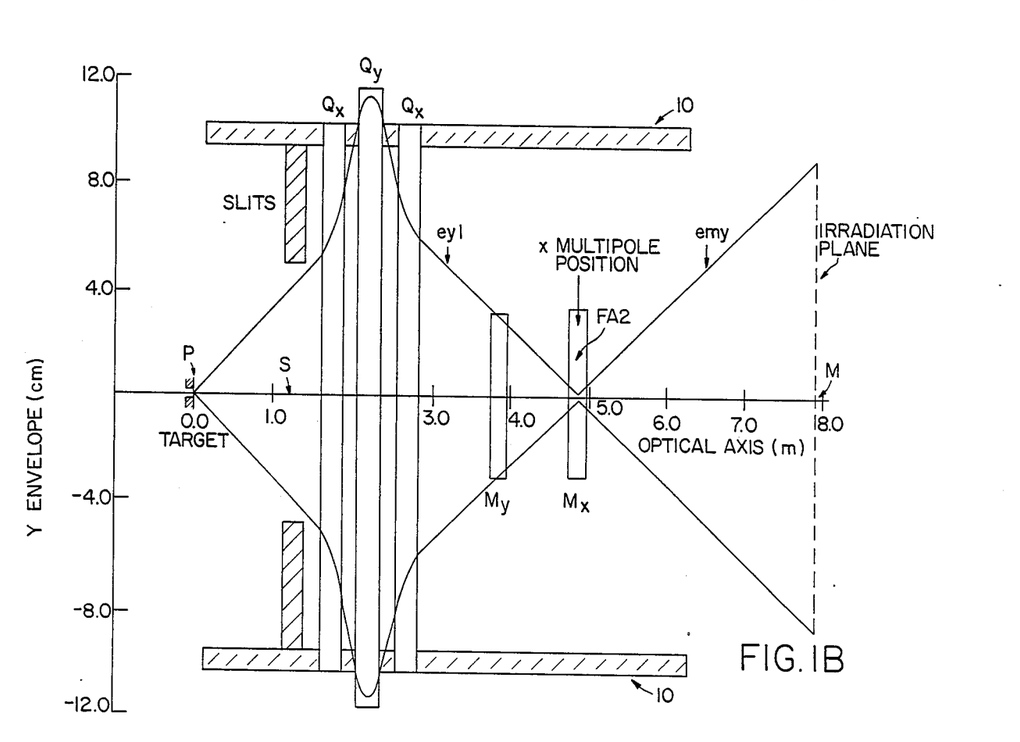
Figure 2A:
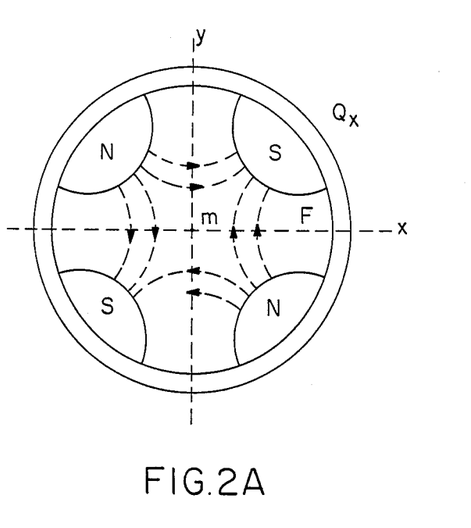
FIGS. 2A and 2B are end cross-sectional views showing the quadrupole magnet sets Qx and Qy for initial beam focussing by fields F.
Figure 2B:
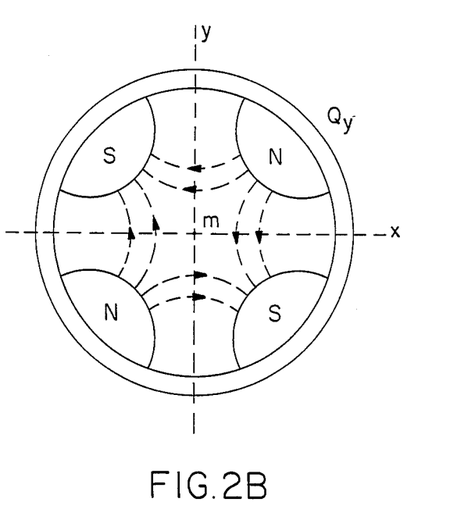
Figure 3A:
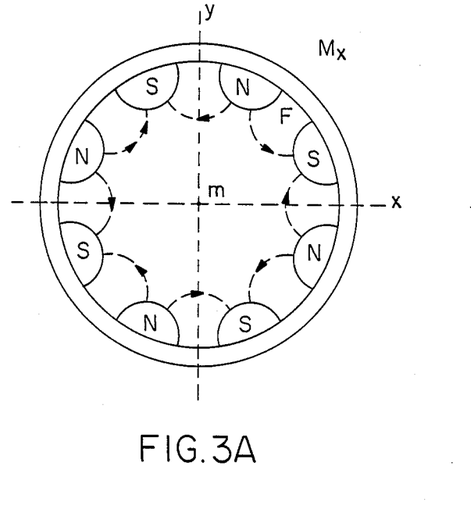
FIGS. 3A and 3B are end cross-sectional views showing octupole magnet sets Mx and My for beam focussing by fields F.
Figure 3B:
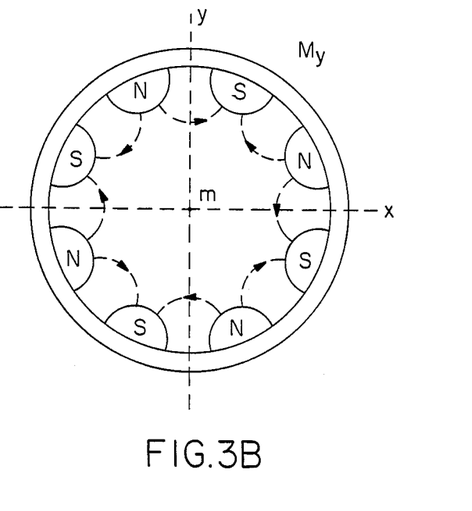

The strengths of the magnetic fields of the quadrupole sets Qx and Qy in the doublet are adjusted so that the waists FA1 and FA2 in the two planes X and Y are displaced from each other along the beam trajectory or axis M. These focal areas FA1 and FA2 are close to the final location of the octupole sets Mx and My, with the actual positions chosen at the waist (minimum beam size areas) FA1 or FA2 of the beam in each dimension after taking into account the effect of the octupole sets Mx and My.

Figure 4A:
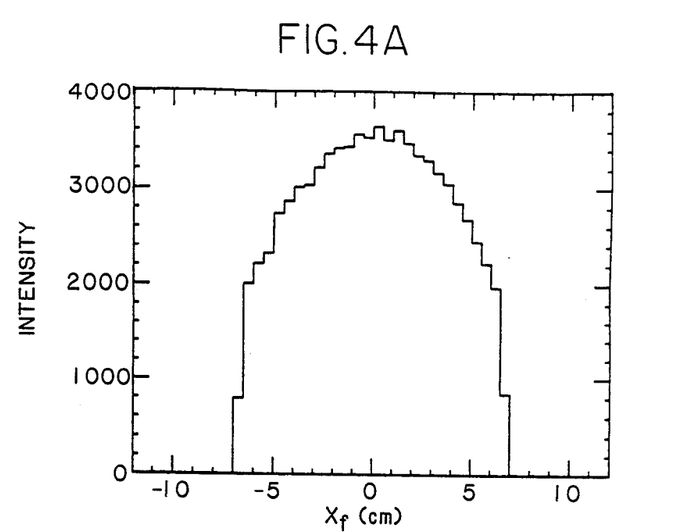
FIGS. 4A to 4D are graphs which show projections of the particle distributions on the X and Y axes for an initial distribution of a uniformly populated ellipse in X−theta and Y−phi phase spaces where theta is the angle in the horizontal plane and phi is the angle in the vertical plane.
Figure 4B:
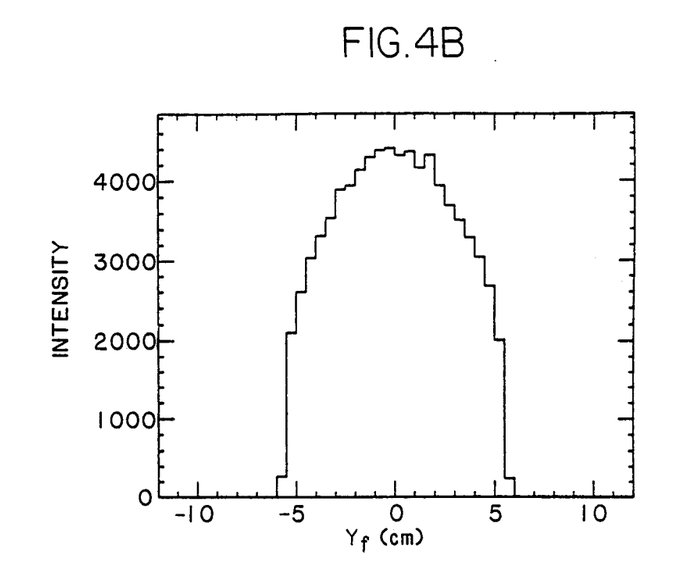

FIGS. 4A and 4B show the projection of the particle intensity on the X axis and on the Y axis at the irradiation position with the octupole sets Mx and My turned off. These were obtained from a randomly selected set of rays within the initial phase space distribution of a uniformly populated ellipsoid, as calculated in the code TURTLE (D. Cary, 'TURTLE', Fermi National Accelerator Laboratory, report 64-2041.000). It is clearly seen that the peaked nature of the distributions is unaffected as it travels through the system.

Figure 4C:
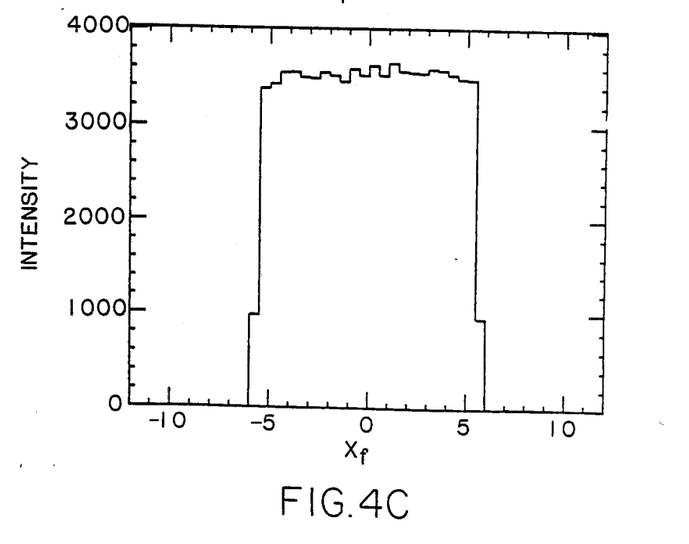
Figure 4D:
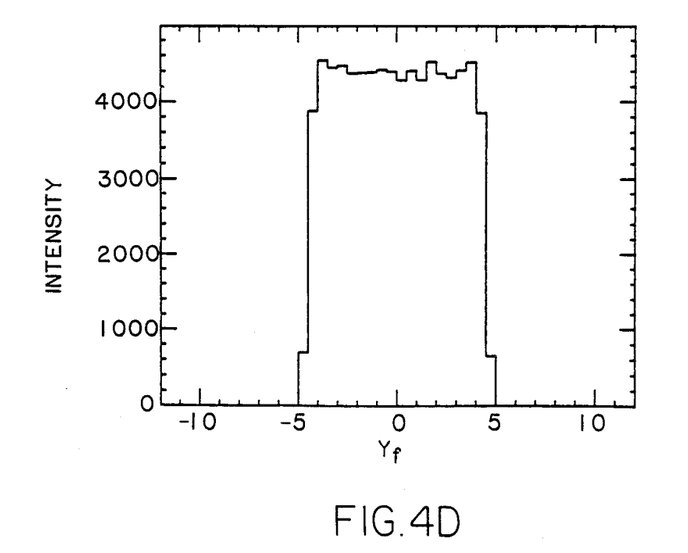
Figure 5A:
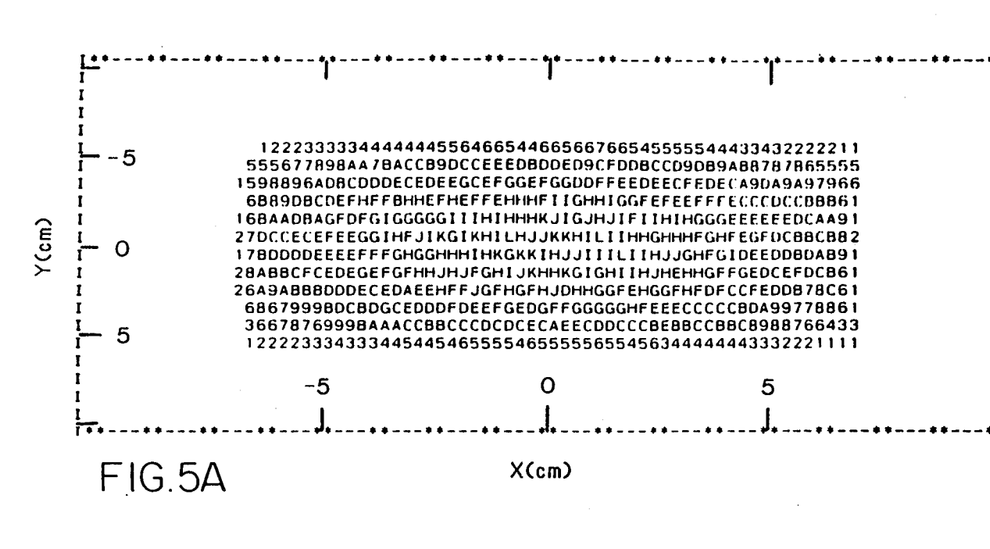
FIG. 5 shows density plots of the particle distribution represented in FIG. 4 in the x-y plane. The number of particles is represented in the figure by numerals or letters, with 1=one to ten, 2=11 to 20, 3=21 to 30, . . ., 9=81-90, A=91 to 100, B=101-110, etc. The distribution in 5A is with no octupoles. The distribution in 5B shows the effect of the octupoles.
Figure 5B:
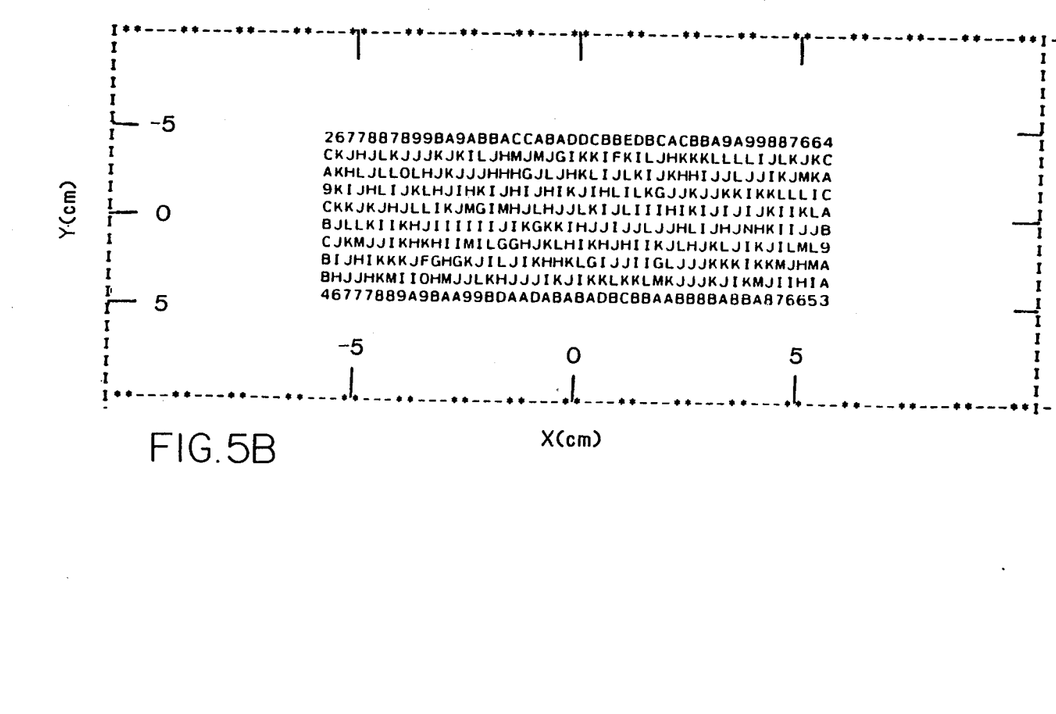
Figure 6A:
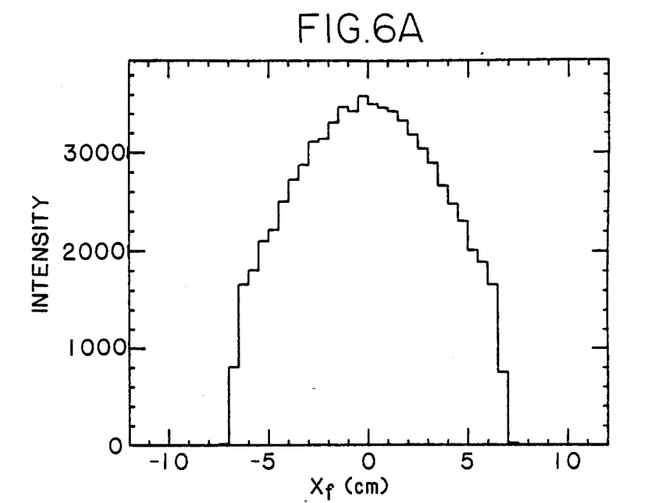
FIGS. 6A to 6D are computer generated graphs showing projections of the particle distributions on the X and Y axes for an initial distribution which is Gaussian.
Figure 6B:
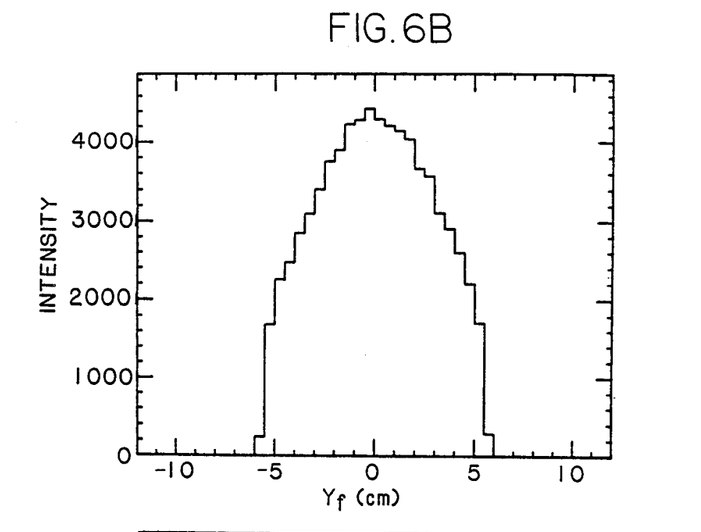
Figure 6C:
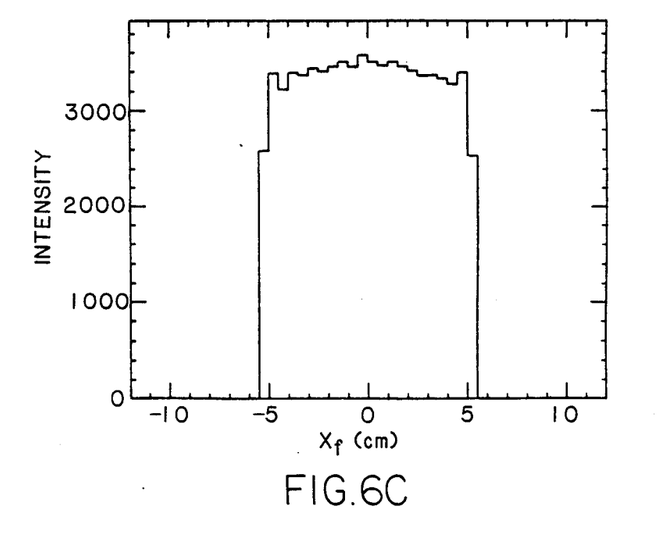
Figure 6D:
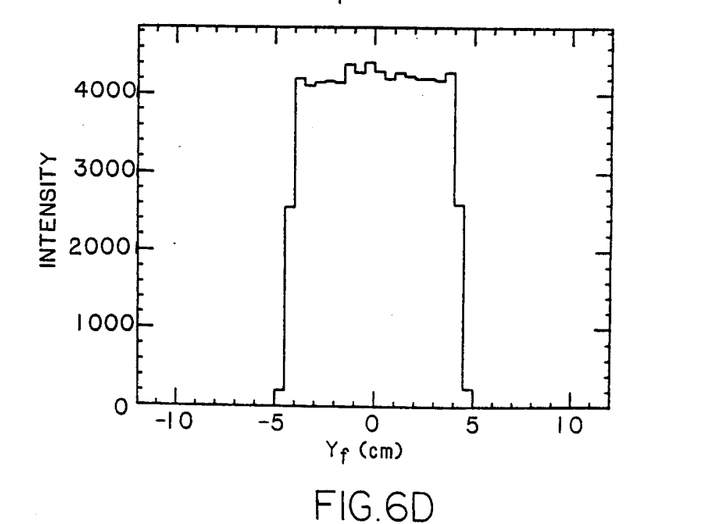

In FIGS. 4C and 4D the two octupole sets Mx and My have been turned on to the appropriate values for flattening the two dimensional or cross-sectional particle intensity distribution. Since the fields required in the octupole sets Mx and My can be quite large, the working apertures can be chosen to reduce the required field strength at the poles and the cost of the lenses. The envelopes emy and emx following the octupole sets Mx and My have been slightly reduced in size. The role of the octupole sets Mx and My in flattening the particle distributions is clearly demonstrated by the calculation of the Gaussian distribution on the measuring plane shown in FIGS. 4A and 4B. In FIG. 4C the homogeneity is better than 10% for a beam which includes about 80% of the initial beam. FIG. 5 shows the density plots of the particle distribution as previously discussed. FIG. 6D shows a similar result for a Gaussian initial distribution shown in FIG. 6B, with 73% of the initial particles. The physical orientations of the octupole sets Mx and My are the same at both positions, but their magnetic fields have opposite signs, since, depending on the plane of action, they are placed ahead and following the respective beam waists FA1 and FA2. The action of the octupole sets Mx and My are essentially independent of each other in view of their placements at the waists FA1 and FA2. Because of the strong effect of the octupole sets Mx and My on the phase space, it is best to place them close to the end of the transport system. The magnetic field strength of the octupoles Mx and My depend on the absolute value of the width of the distribution, and need to be adjusted accordingly.

The size of the irradiated field can be controlled by adjusting the distances and by the size of the aperture at the slit ahead of the first quadrupole. Proper limits of the field can be assured by a mask (not shown) at the irradiation location. For very small size irradiation areas, other procedures which include a smaller object slit as well as the use of an initial scatterer of lower atomic number Z may be used (not shown).

In the previous example for the flattening of symmetric distributions, magnetic octupole sets Mx and My were used as the non-linear elements. In general various combinations of high order multipole sets can be used, depending upon the symmetry and shape of the initial particle distribution, preferably between six (6) and twenty (20) pole sets.

The method and apparatus allows the use of higher order magnetic elements to alter beam intensity distributions. The method is simple and economical.

Numerous variations will occur to those skilled in the art and it is intended that the foregoing description only be illustrative of the present invention.

We claim:

1. A magnetic optical beam homogenizing and focussing apparatus for charged particle beams which comprises:
   (a) holder means which mounts on a source of accelerated charged particles which are scattered outward in a gaussian-like angular distribution from a longitudinal axis from the source, wherein a X and a Y axis are defined perpendicular to the longitudinal axis;
   (b) beam trnsport magnetic lens sets positioned on the holder means around the longitudinal axis, such that the charged particles are focussed towards and cross the longitudinal axis to define a focal area on the axis wherein the focal area of the beam viewed on the X axis is at a different part of the longitudinal axis than the focal area of the beam viewed on the Y axis; and
   (c) at least two multipole magnet sets each having at least 6 poles mounted on the holder means around the longitudinal axis at each of the focal areas on the X and Y axis, wherein the multipole magnet sets depending upon the number of poles, make specific changes to the direction of the particles according to the position of the particles within the multipole magnet sets to thereby homogenize and focus the beam.

2. The method of claim 1 wherein each of the multipole magnet sets have between 6 and 20 poles.

3. The apparatus of claim 1 wherein each of the multipole magnet sets have 8 poles.

4. A method for homogenizing and focussing a beam of charged particles on a surface to be irradiated which comprises:
   (a) providing a holder means mounted on a point source of accelerated charged particles which are scattered outward in a gaussian angular distribution from a longitudinal axis from the source wherein a X and a Y axis are defined perpendicular to the logitudinal axis; beam transport magnetic lens sets positioned on the holder means around the longitudinal axis, such tha the charged particles are focussed towards and cross the longitudinal axis to define a focal area on the axis wherein the focal area of the beam viewed on the X axis is at a different part of the longitudinal axis than the focal area of the beam viewed on the Y axis; and at least two multipole magnet sets having at least 6 poles mounted on the holder means around the longitudinal axis at each of the focal areas on the X and Y axis, wherein the multipole magnet sets depending upon the number of poles, make specific changes to the direction of the particles according to the position of the particles within the multipole magnet sets to thereby homogenize and focus the beam;
   (b) providing the homogenized and focussed beam on the surface to be irradiated.

5. The method of claim 4 wherein each of the multipole magnet sets have between 6 to 20 poles.

6. The method of claim 3 wherein each of the multipole magnet sets have 8 poles.

* * * * *

UNITED STATES PATENT AND TRADEMARK OFFICE
CERTIFICATE OF CORRECTION

PATENT NO. : 4,736,106
DATED : April 5, 1988
INVENTOR(S) : Edwin Kashy and Bradley M. Sherrill It is certified that error appears in the above—identified patent and that said Letters Patent is hereby corrected as shown below:

Column 2, line 31, "trasversing" should be --traversing--.

Column 5, line 24, "trnsport" should be --transport--.

Column 6, line 18, "tha" should be --that--.

Column 6, line 35, "to" should be --and--.

Signed and Sealed this

Twenty-eighth Day of February, 1989

Attest:

DONALD J. QUIGG

Attesting Officer        Commissioner of Patents and Trademarks